(12) United States Patent
Sadek

(10) Patent No.: US 10,493,206 B1
(45) Date of Patent: Dec. 3, 2019

(54) DENTAL ANESTHETIC BUFFER ASSEMBLY

(71) Applicant: Yasser Sadek, San Diego, CA (US)

(72) Inventor: Yasser Sadek, San Diego, CA (US)

(*) Notice: Subject to any disclaimer, the term of this patent is extended or adjusted under 35 U.S.C. 154(b) by 78 days.

(21) Appl. No.: 15/204,817

(22) Filed: Jul. 7, 2016

Related U.S. Application Data

(60) Provisional application No. 62/194,807, filed on Jul. 20, 2015.

(51) Int. Cl.
*A61M 5/28* (2006.01)
*A61C 19/08* (2006.01)
*A61M 19/00* (2006.01)

(52) U.S. Cl.
CPC ............ *A61M 5/284* (2013.01); *A61C 19/08* (2013.01); *A61M 5/288* (2013.01); *A61M 19/00* (2013.01)

(58) Field of Classification Search
CPC .... A61M 5/284; A61M 5/288; A61M 5/2066; A61M 5/16827; A61C 19/08
See application file for complete search history.

(56) References Cited

U.S. PATENT DOCUMENTS

| | | | |
|---|---|---|---|
| 2012/0226238 A1* | 9/2012 | Davies | A61M 5/284 604/191 |
| 2013/0115569 A1* | 5/2013 | Lambert | A61M 5/2448 433/90 |
| 2015/0053305 A1* | 2/2015 | Davidian | A61M 5/31591 141/2 |

* cited by examiner

*Primary Examiner* — Rebecca E Eisenberg
*Assistant Examiner* — Tasnim Mehjabin Ahmed
(74) *Attorney, Agent, or Firm* — Law Office of Glenn R. Smith; Glenn R. Smith

(57) ABSTRACT

A dental anesthetic buffer assembly advantageously attaches to carpule-loaded syringe in the same manner as a standard disposable needle. The dental anesthetic buffer assembly, however, incorporates a pH-raising buffer that advantageously dissolves into and mixes with the carpule anesthetic during injection, in lieu of pre-mixing the buffer and anesthetic prior to injection.

3 Claims, 10 Drawing Sheets

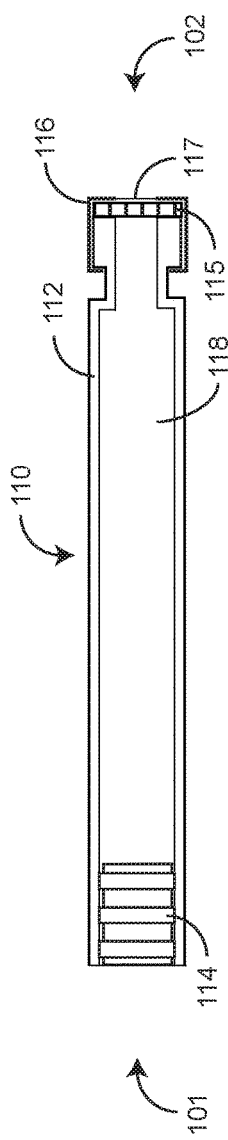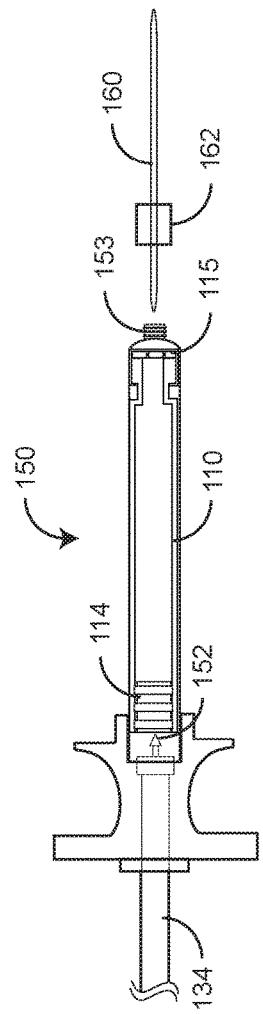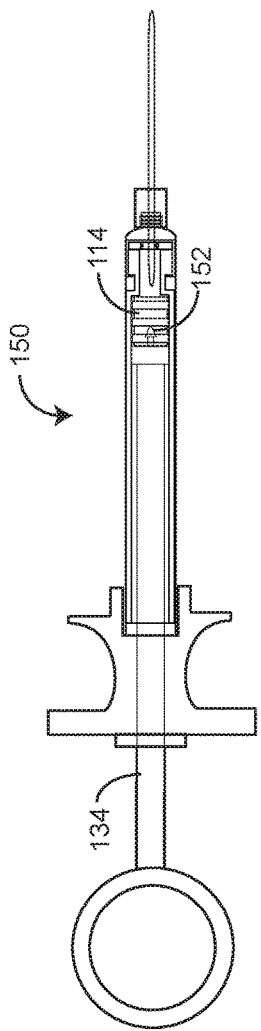
FIG. 1A (Prior Art)
FIG. 1B (Prior Art)
FIG. 1C (Prior Art)

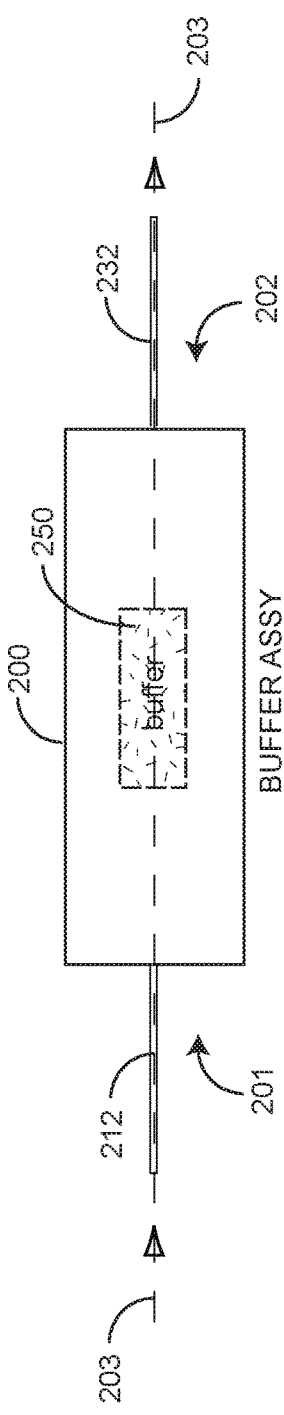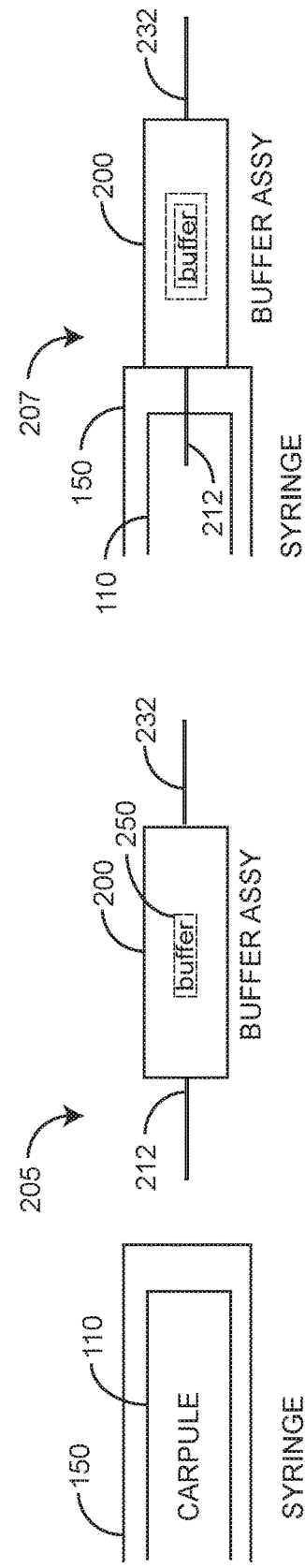
FIG. 2A
FIG. 2B
FIG. 2C

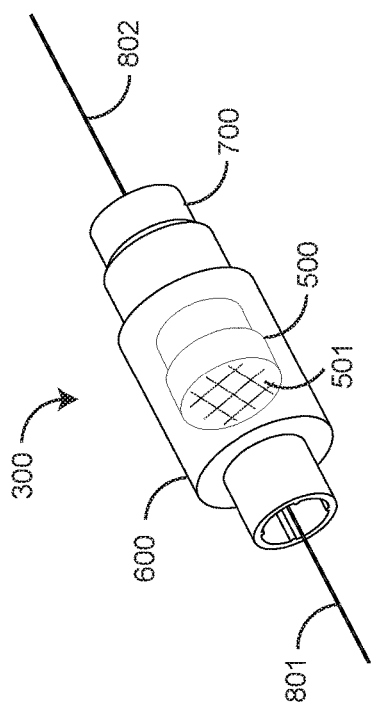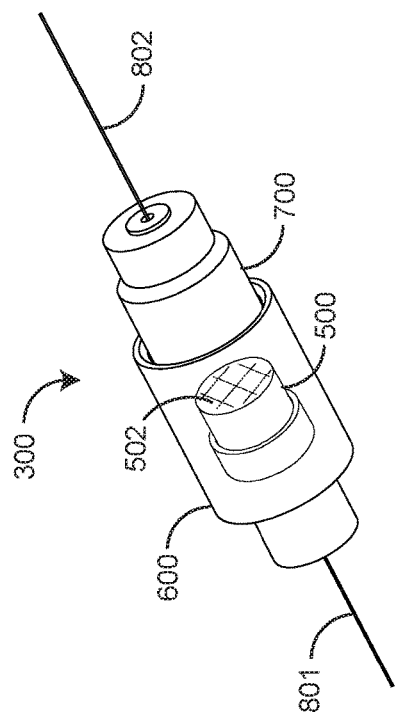
FIG. 4A
FIG. 4B

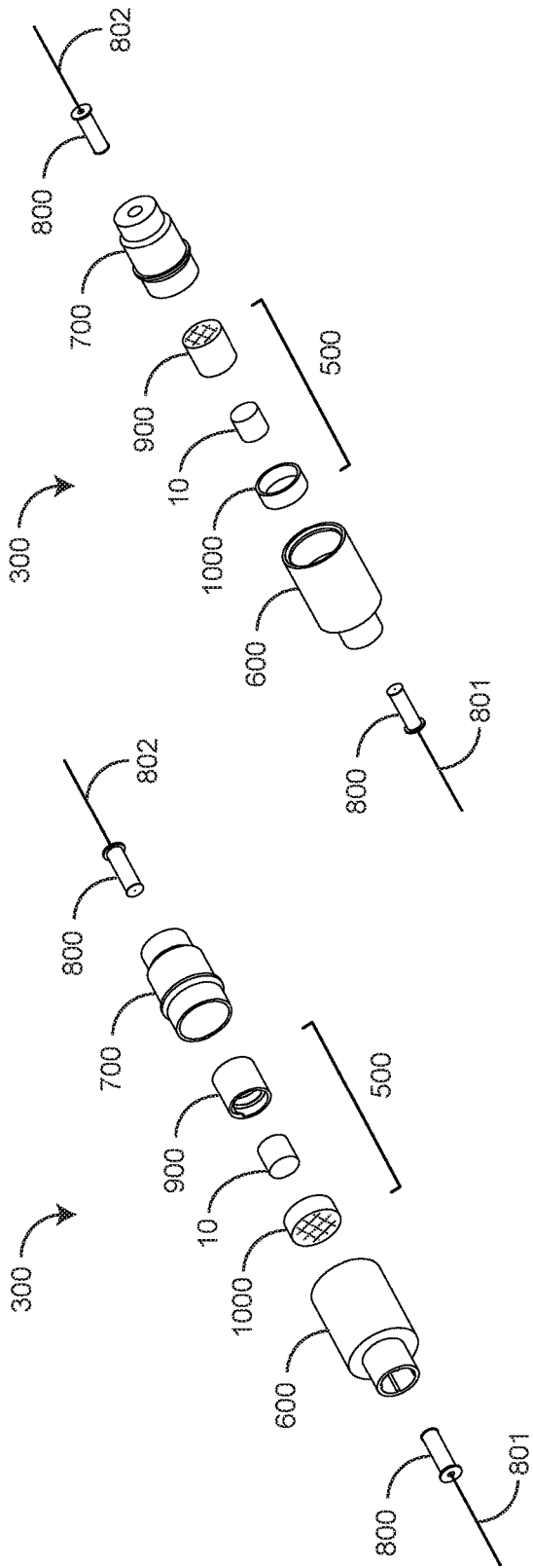
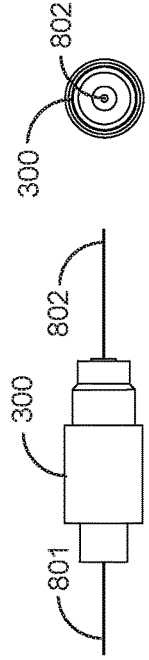
FIG. 5A
FIG. 5B
FIG. 5C  FIG. 5D  FIG. 5E

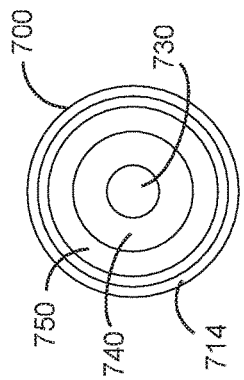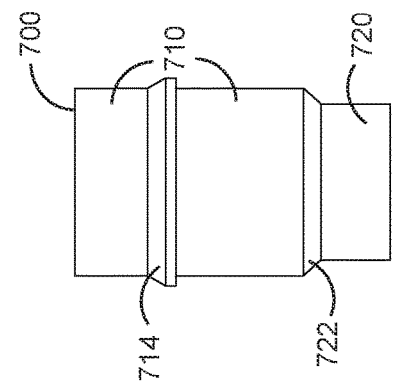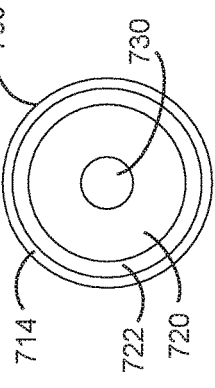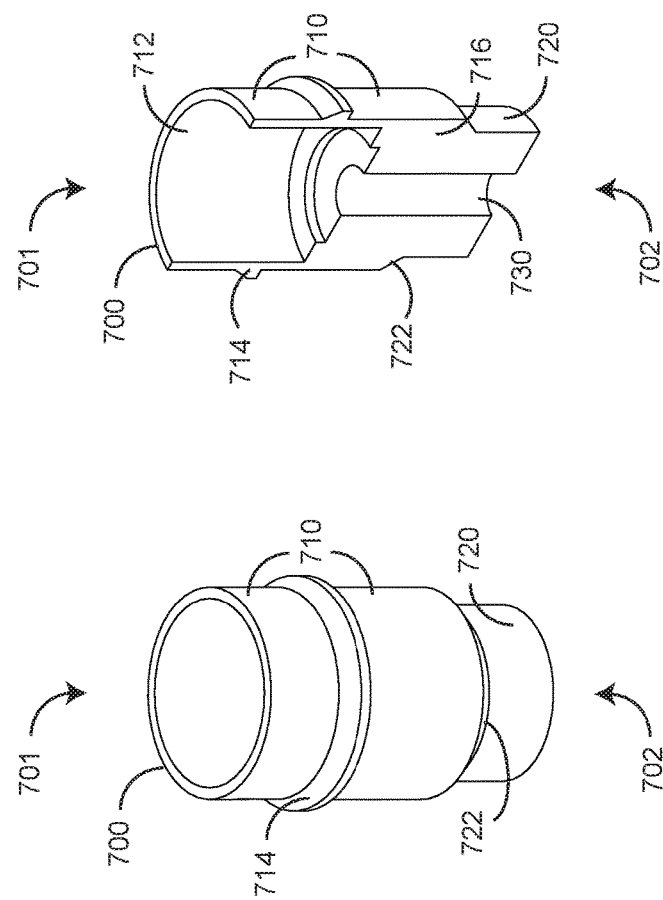

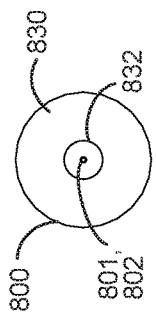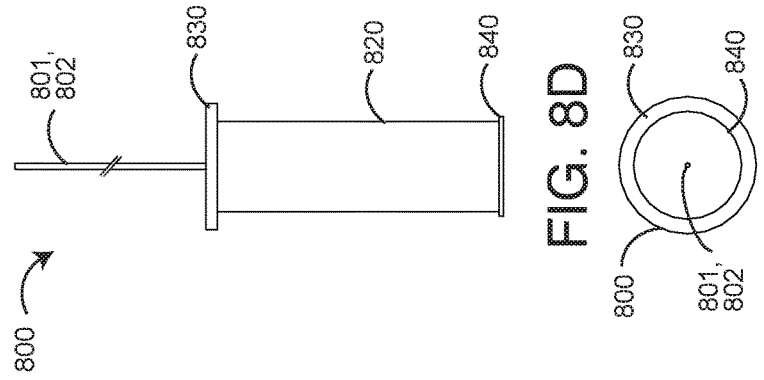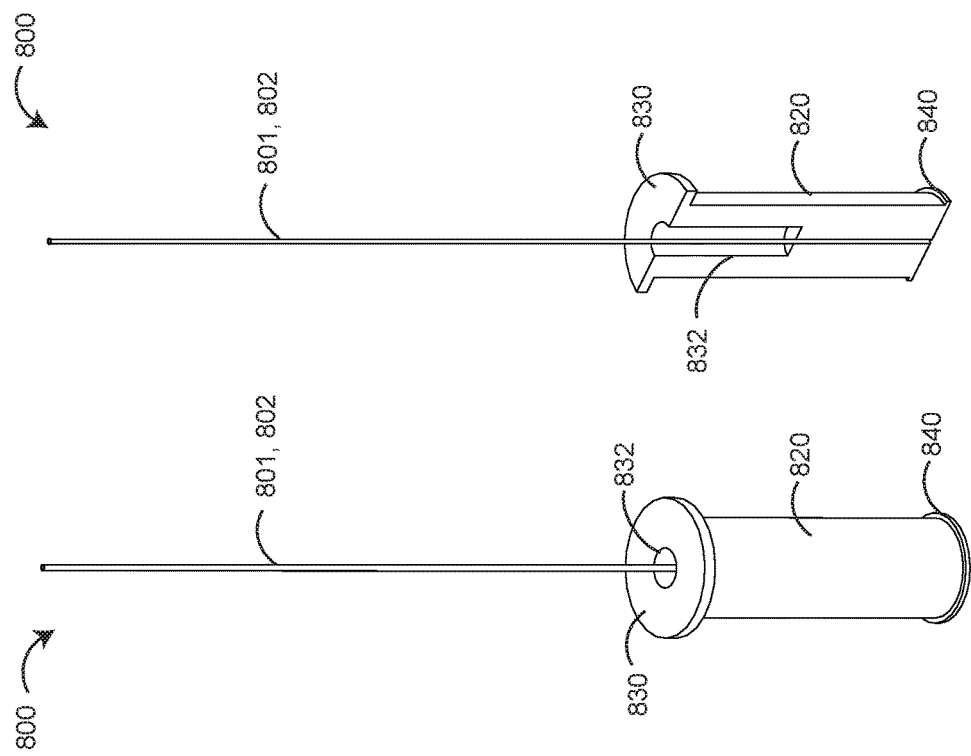

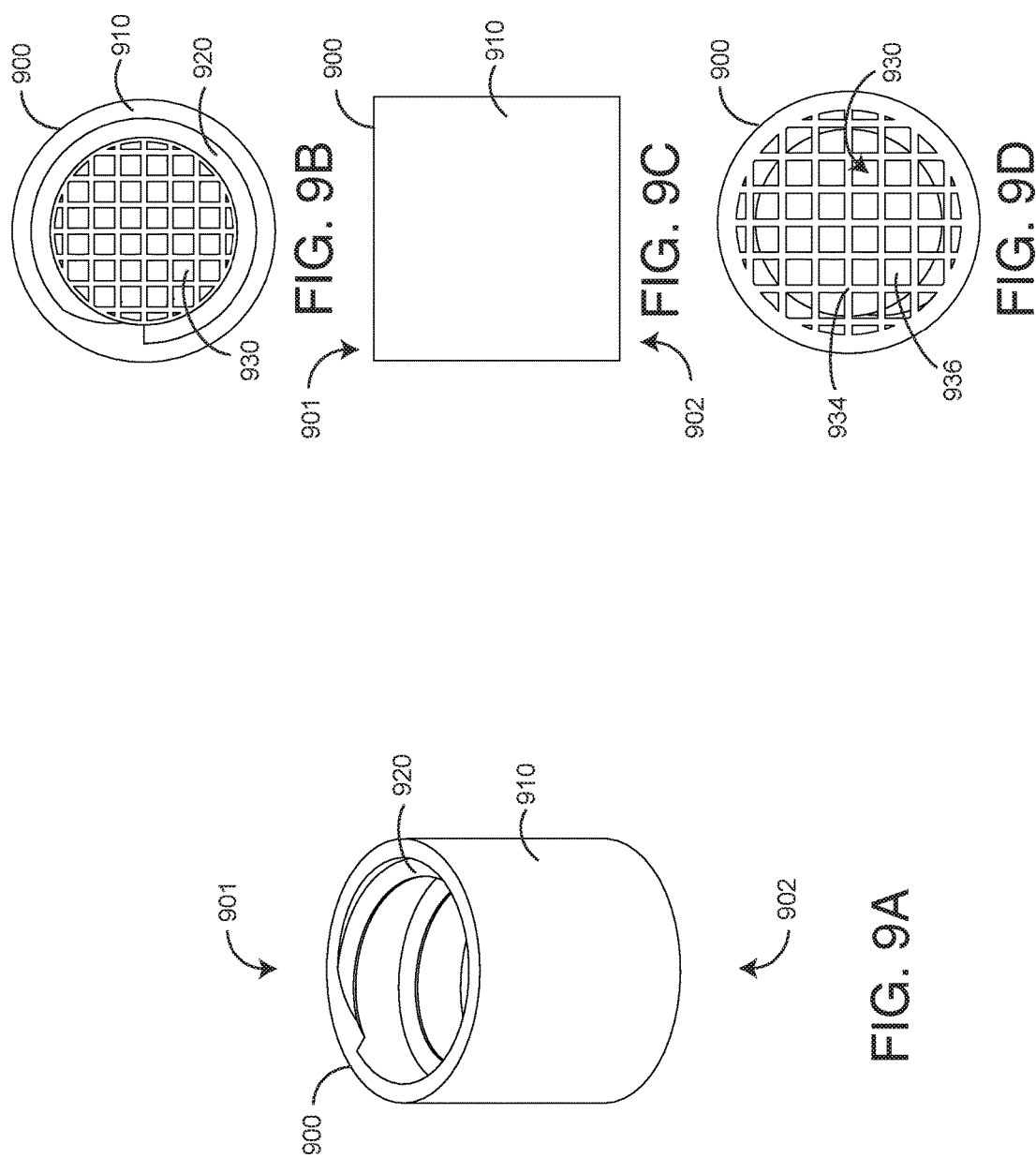

US 10,493,206 B1

DENTAL ANESTHETIC BUFFER ASSEMBLY

PRIORITY CLAIM TO RELATED PROVISIONAL APPLICATIONS

The present application claims priority benefit under 35 U.S.C. § 119(e) to U.S. Provisional Patent Application Ser. No. 62/194,807 titled Disposable Anesthetic-Buffering Needle, filed Jul. 20, 2015 and hereby incorporated in its entirety by reference herein.

INCORPORATION BY REFERENCE OF RELATED CASES

The present disclosure is generally related to U.S. patent application Ser. No. 14/662,231 titled Dental Anesthetic Buffer System, filed Mar. 18, 2015 and hereby incorporated in its entirety by reference herein.

BACKGROUND OF THE INVENTION

Medical personnel, including dentists and physicians, often inject an anesthetic into a patient prior to performing various procedures, such as drilling cavities, preparing teeth for crowns and tooth extractions, to name a few.

FIGS. 1A-C illustrate a prior art anesthetic carpule 110 (FIG. 1A), a pre-injection dental syringe 150 (FIG. 1B) and corresponding syringe needle 160 (FIG. 1B) and a post-injection dental syringe 150 (FIG. 1C). As shown in FIG. 1A, a carpule 110 has a glass or plastic tube 112 having a first end 101 and an opposite second end 102. A rubber stopper 114 seals the first end 101 and a diaphragm 115 held in place by an aluminum cap 116 seals the second end 102. An anesthetic 118 is contained in the tube 112 between the sealed ends 101, 102. An aperture 117 in the cap 116 allows needle access to the anesthetic 118 via a punctured hole in the diaphragm 115.

As shown in FIG. 1B, the carpule 110 is loaded into a syringe 150 for injection. A needle 160 is inserted through the diaphragm 115 and held in place with a needle cap 162 pressed over a threaded syringe port 153. A plunger 154 engages the rubber stopper 114 via a harpoon 152 piercing the exposed end of the stopper. The plunger 154 is used to eject any air from the needle prior to insertion of the needle 162 into a patient tissue site. The harpoon 152 allows the plunger to slightly withdraw the stopper so as to aspirate the syringe, insuring the needle is not in a blood vessel. As shown in FIG. 1C, after aspiration, the plunger drives the rubber stopper down the carpule, injecting the carpule contents into the tissue site.

SUMMARY OF THE INVENTION

Numbing solutions, such as lidocaine, sting when injected, due to a low (acidic) pH. In order to reduce the sting of a dental anesthetic, a buffering solution, such as sodium bicarbonate, can be mixed into the anesthetic during injection so as to raise the pH (lower the acidity) of the anesthetic. This reduces injection pain and allows the anesthetic to take effect quicker. The buffer also ionizes the anesthetic molecules so that they immediately act on a patient's nerve cells. Further, the buffer reaction with the anesthetic produces carbon dioxide, which adds to the anesthetic effect. Advantageously, the buffering process occurs during injection using a standard dental syringe. In an embodiment, the buffer is sodium bicarbonate. In an embodiment, the buffer assembly mixes of sodium bicarbonate with the anesthetic.

A dental anesthetic buffer assembly (DABA) advantageously attaches to, and after use is removed from, a carpule-loaded syringe in the same manner as a standard disposable needle. The DABA needle, however, incorporates a solid pH-raising buffer that advantageously dissolves into and mixes with the anesthetic during injection. This is unlike other buffering devices that require pre-mixing of buffer and anesthetic prior to injection.

One aspect of dental anesthetic buffer assembly is replacement for a standard disposable needle that removably-mounts to a syringe for ejecting an anesthetic solution into a person. The dental anesthetic buffer assembly needle has a generally cylindrical syringe-side needle base. That needle base has a first end that is configured to removably-attach to a standard syringe needle-mount and a second end that accepts a first needle assembly. A generally cylindrical patient-side needle base has a first end that interleaves with the syringe-side needle base and an opposite second end that accepts a second needle assembly. A buffer holder has an open end that receives a solid buffer and a grill-end that passes injection fluid through the buffer holder. A buffer cap has an open end that mates with the buffer holder so as to enclose the solid buffer and a grill-end that passes injection fluid through the buffer holder. The buffer holder has a spiral thread disposed around an inside wall of the buffer holder so as to swirl the injection fluid around the solid buffer and more readily dissolve the buffer and mix it with the injection fluid.

Another aspect of a dental anesthetic buffer assembly is a receiver that removably attaches to a needle mount of a syringe. An injector is in mechanical communications with the receiver. A buffer is disposed between the receiver and the injector. A fluid path between the receiver and the injector allows anesthetic to pass between the needle mount and the injector. A fluidly-transmissive mixer encloses the buffer and is disposed within the fluid path so as to facilitate mixing the buffer with anesthetic solution ejected from the syringe. The receiver has a generally cylindrical mount housing, a generally cylindrical receiver housing extending from the mount housing, a needle aperture axially-disposed within the mount housing and a needle assembly disposed within the needle aperture. The needle assembly has a generally cylindrical needle base and an injection needle extends from the needle base. The mixer has a buffer holder and a buffer cap interleaved with the buffer holder so as to create a buffer chamber. The mount housing has a first end and a second end. The mount housing first end has a generally cylindrical mount fixture that removably attaches to a syringe needle mount. The mount housing second end has a generally cylindrical mount housing chamber that accepts at least a portion of the mixer. The mount housing interleaves with an injector housing so as to fully enclose the mixer. The needle fixedly attaches within the mount housing first end so as to pierce a carpule seal when the buffer assembly is attached to the syringe needle mount. The needle provides fluid communications between carpule and buffer holder. The injector has a generally cylindrical injector housing that interleaves with the mount housing so as to enclose the mixer.

BRIEF DESCRIPTION OF THE DRAWINGS

FIGS. 1A-C are side carpule, transparent side pre-injection and transparent side injection views, respectively, of a prior art carpule and corresponding dental syringe and needle;

FIGS. 2A-C are general block diagram views of an advantageous dental anesthetic buffer assembly including enlarged, un-mounted syringe and mounted syringe side-views, respectively;

FIGS. 4A-B are perspective receiver-end and injector-end views, respectively, of an dental anesthetic buffer assembly;

FIGS. 5A-E are receiver-end exploded perspective, injector-end exploded perspective, receiver-end, side and injector-end views, respectively, of a dental anesthetic buffer assembly;

FIGS. 7A-E are a perspective, cutaway-perspective, open-end, side and closed-end views, respectively, of an injector embodiment;

FIGS. 8A-E are perspective, cutaway perspective, needle end, side and base end views, respectively, of a needle assembly; and FIGS. 9A-D are perspective, open-end, side and grill-end views, respectively, of a buffer holder.

DETAILED DESCRIPTION OF THE PREFERRED EMBODIMENTS

Figure 3A:
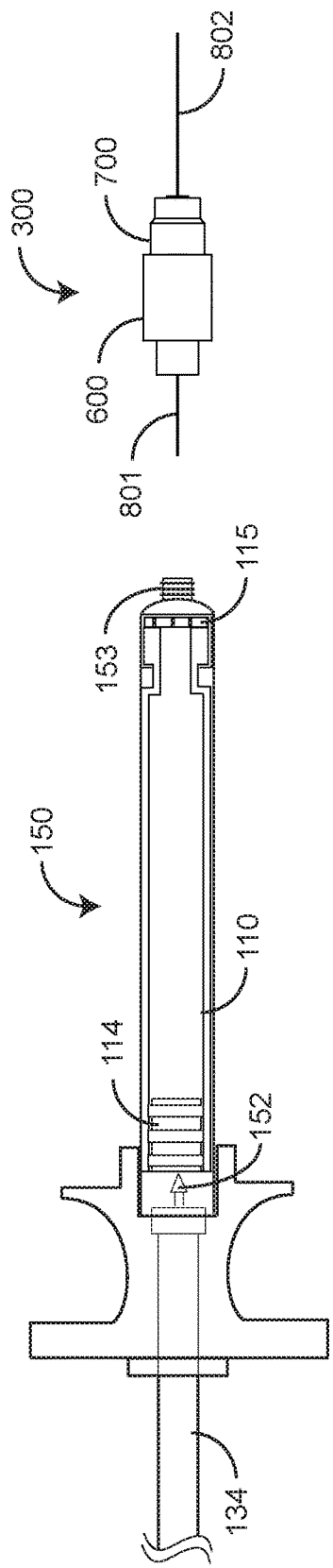
FIGS. 3A-B are an unattached-syringe side view and an attached-syringe side view, respectively, of an advantageous dental anesthetic buffer assembly embodiment.

FIGS. 2A-C generally illustrate an advantageous dental anesthetic buffer assembly (DABA). DABA 200 removably mounts to a standard syringe in the same manner as a standard injection needle so as to inject buffered carpule fluid into a patient. Likewise DABA 200 may be disposed of after a single use in the same manner as a standard injection needle.

As shown in FIG. 2A, a buffer assembly embodiment 200 has a buffer 250 disposed between a receiver end 201 and an injector end 202. A carpule needle 212 and a injector needle 232 provide a fluid path 203 from a carpule 110 (FIG. 2B) into the receiver end 201 and out of an injector end 202. A buffer 250 disposed between the ends 201, 202 combines with anesthetic contained in the carpule 110 as the syringe 150 forces the anesthetic through the injection path 203 and into a patient. As shown in FIG. 2B, in an un-mounted position 205, the buffer assembly 200 is positioned proximate the syringe needle mount (not shown) so that the carpule needle 212 aligns with a needle aperture (not shown) disposed through needle mount.

As shown in FIG. 2C, in a mounted position 207, the buffer assembly 200 is secured to the syringe 150 as the carpule needle 212 is disposed through the needle mount (not shown) and into the syringe 150, piercing the carpule membrane 115 (FIG. 1B). In various embodiments, described below, DABA 200 may have separate receiver, injector and mixer components that interleave or abut together and are fixedly secured together via glue, weld, screw, twist lock or other joint so as to enclose the mixer within the completed buffer assembly.

Figure 3B:
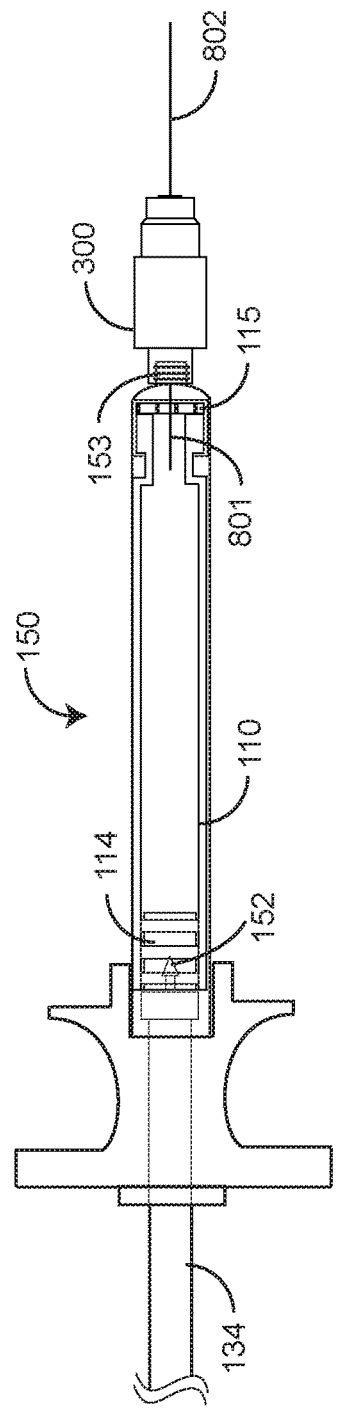
Figure 6C:
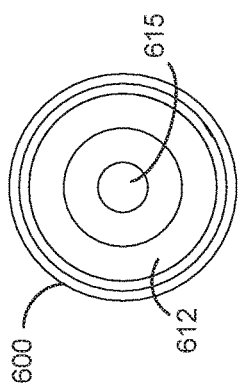
FIGS. 6A-E are perspective, cutaway-perspective, open-end, side and closed-end views, respectively, of a receiver embodiment.
Figure 6D:
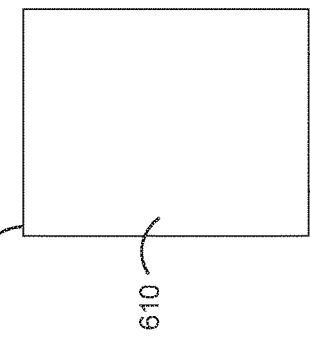
Figure 6E:
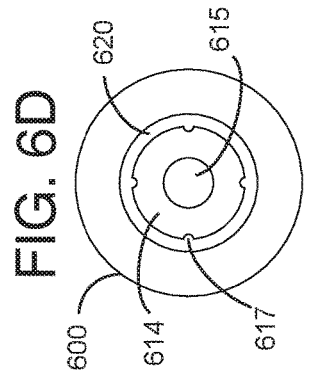
Figure 6B:
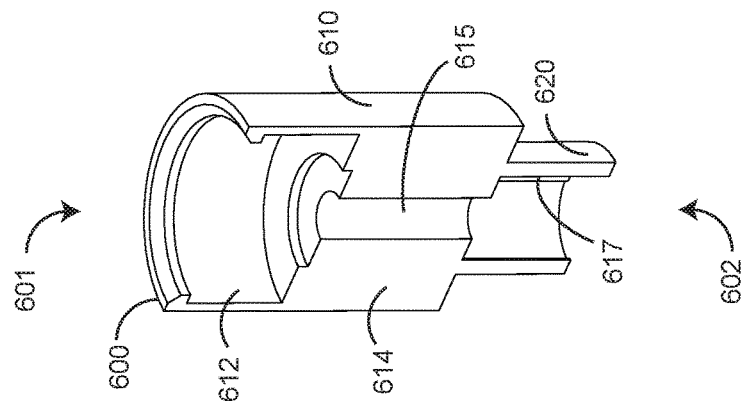
Figure 6A:
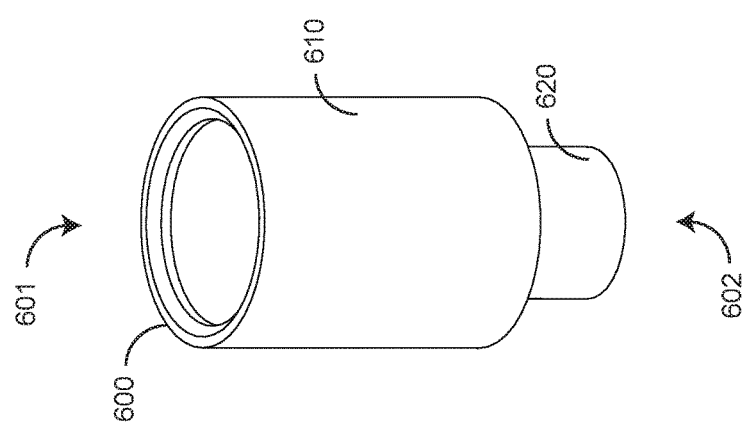
Figure 10B:
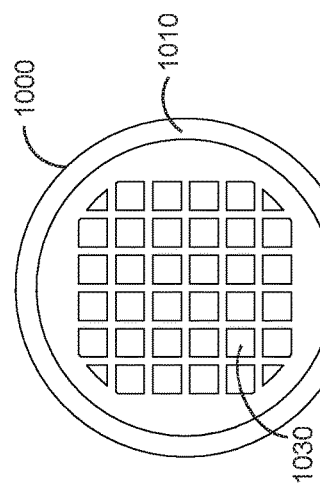
FIGS. 10A-D are perspective, open-end, side and grill-end views, respectively, of a buffer cap.
Figure 10C:
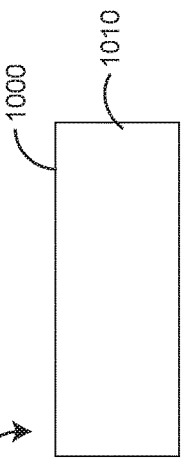
Figure 10D:
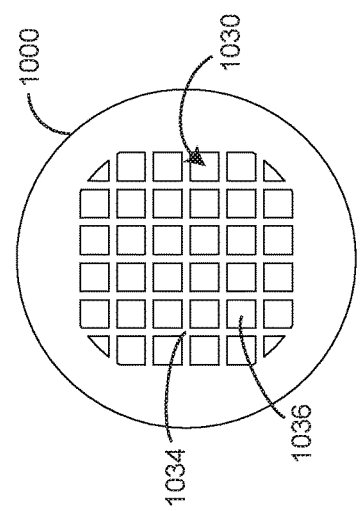
Figure 10A:
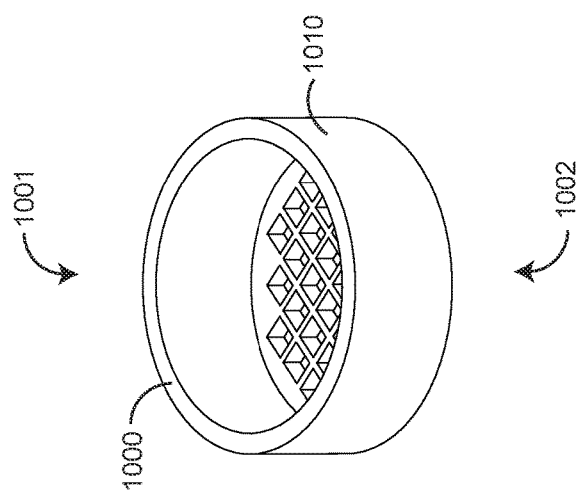

FIGS. 3-5 generally illustrate an advantageous dental anesthetic buffer assembly (DABA) 300 embodiment. As shown in FIGS. 3A-B, the DABA 300 has a receiver 600 and injector 700 that enclose a mixer (not visible) containing a buffer (not visible). The receiver 600 has an open end that securely fits over a threaded syringe port 153 so as to attached the DABA 300 to the syringe 150. A first needle 801 extends from the receiver 600 so as to penetrate the carpule membrane 115 and provide a fluid path for the anesthetic from the receiver 600 to the injector 700. A second needle 802 extends from the injector 700 so as to provide a fluid path for the anesthetic from the injector 700 to the patient.

As shown in FIGS. 4A-B, a dental anesthetic buffer assembly embodiment 300 has a receiver 600 and an injector 700. The receiver 600 and injector 700 both enclose a mixer 500 that contains a buffer 10 (FIGS. 5A-B). A carpule needle 801 extends from the receiver 600 and an injection needle 802 extends from the injector 700. The mixer 500 has a first end 501 generally disposed proximate an interior portion of the carpule needle 801 a second end 502 generally disposed proximate an interior portion of the injection needle 802. The first and second mixer ends 501, 502 are screened, grilled, meshed, gridded or otherwise filtered so that the buffer within is generally mixed with and dissolved by anesthetic flow through the mixer 500 before reaching the injection needle 802

As shown in FIGS. 5A-E a dental anesthetic buffer assembly embodiment 300 has a receiver 600 and injector 700 that interleave so as to enclose the mixer 500 and corresponding buffer 10. Both the receiver 600 and the injector 700 accept a needle assembly 800. The mixer 500 has a base 900 and a cap 1000, which interleave so as to enclose a solid buffer 10. In an embodiment, the buffer 10 dissolves in an advantageous swirl-mix action as the syringe plunger 134 (FIGS. 3A-B) forces anesthetic fluid from the carpule 110 (FIGS. 3A-B), through the carpule needle 801 and into the mixer 500. The now-buffered anesthetic flows from the mixer 500 and traverses the injector 700 through the injection needle 802 and into a patient.

FIGS. 6A-E illustrate a receiver embodiment 600 having a relatively long, large-diameter cylinder 610 disposed proximate a first end 601 mated with a relatively short, small-diameter cylinder 620 disposed proximate a second end 602. The large-diameter cylinder 610 has hollow portion 612 proximate the first end 601 and a solid portion 614 distal the first end 601. An aperture 615 is centrally disposed through the solid portion 614 so as to receive a needle assembly 800 (FIGS. 8A-E). The small-diameter cylinder 620 is advantageously configured as a syringe mount, having a plurality of protrusions 617 running the length of the inside of the small-diameter cylinder 620. The small-diameter cylinder 620 removably fits over a syringe port 153 (FIG. 1B), secured by the protrusions 617, so as to removably attach the buffer assembly 300 (FIGS. 1A-B) to a syringe 150 (FIGS. 1A-B). The receiver first end 601 interleaves over the injector first end 701 to form the buffer assembly 300 (FIGS. 3-4) that encloses a mixer 500 (FIGS. 5A-B) containing a buffer 10.

FIGS. 7A-E illustrate an injector embodiment 700 having a relatively long, large-diameter cylinder 710 disposed proximate a first end 701 mated with a relatively short, small-diameter cylinder 720 disposed proximate a second end 702. The large cylinder 710 has hollow portion 712 proximate the first end 701 and a solid portion 716 distal the first end 701. An aperture 730 is centrally disposed through the solid portion 716 so as to receive a needle assembly 800 (FIGS. 8A-E). The small-diameter cylinder 720 has a bevel 722 extending to the large-diameter cylinder 710. A seal 714 encircles the large-diameter cylinder approximately a third of the distance from the first end 701 to the bevel 722. The injector large-diameter cylinder 710 interleaves within the receiver large-diameter cylinder 610 passed the seal 714.

FIGS. 8A-E illustrate a needle assembly 800 having a needle 801, 802 extending from a needle base 820. The needle base 820 is generally cylindrical having a relatively large diameter needle rim 830 and a relatively small diameter base rim 840. The needle rim 830 has a rim aperture 832 extending through the rim 830 and approximately half the length of the base 820. Two needle assemblies 800 are disposed on opposite ends of the buffer assembly 300 (FIGS. 3A-B) so that a first needle 801 extends from the receiver 600 (FIGS. 4A-B) and a second needle 802 extends from the injector 700 (FIGS. 4A-B).

FIGS. 9A-D illustrate buffer holder 900 having a generally cylindrical body 910 having an open first end 901 and a filtering second end 902. A spiral thread 920 is disposed around the inside periphery of the body 910 extending from the first end 901 to the second end 902. In an embodiment, the filtering second end 902 has a matrix 930 of relatively narrow bars 934 forming a plurality of apertures 936. The body 910 is advantageously sized to hold an amount of buffer sufficient to neutralize the acidity of a typical anesthetic injection.

FIGS. 10A-D illustrate a buffer cap 1000 having a generally cylindrical body 1010 having an open first end 1001 and a filtering second end 1002. In an embodiment, the filtering second end 1002 has a matrix 1030 of relatively narrow bars 1034 forming a plurality of apertures 1036. The cap 1010 is advantageously sized to enclose the open first end 901 of the buffer holder 900 so as to hold a buffer.

A dental anesthetic buffer assembly has been disclosed in detail in connection with various embodiments. These embodiments are disclosed by way of examples only and are not to limit the scope of the claims that follow. One of ordinary skill in the art will appreciate many variations and modifications.

What is claimed is:

1. A dental anesthetic buffer assembly comprising:
   a receiver having a syringe mount that is removably disposed over the exterior of a needle mount of a syringe, the receiver extending distal the syringe;
   an injector in mechanical communication with the receiver extending distal the syringe and the receiver;
   a one-piece, solid, cylindrical buffer disposed between the receiver and the injector;
   a fluid path between the receiver and the injector;
   a mixer enclosing the buffer and disposed within the fluid path so as to facilitate mixing the buffer with an anesthetic as the anesthetic is elected from the syringe; and
   the mixer having a buffer holder and a buffer cap interleaved with the buffer holder so as to create a buffer chamber.

2. The dental anesthetic buffer assembly according to claim 1, wherein the buffer holder and buffer cap comprise grids that pass dissolved portions of the buffer.

3. The dental anesthetic buffer assembly according to claim 2 wherein the buffer holder comprises a spiral thread disposed within the interior of the buffer holder so as to mix the buffer and the anesthetic as the anesthetic is injected through the buffer holder and the buffer cap.

* * * * *